United States Patent [19]

Ellingboe

[11] Patent Number: 5,466,692
[45] Date of Patent: Nov. 14, 1995

[54] SUBSTITUTED PYRIDOPYRIMIDINES AND ANTIHYPERTENSIVES

[75] Inventor: John W. Ellingboe, Princeton, N.J.

[73] Assignee: American Home Products Corporation, Madison, N.J.

[21] Appl. No.: 179,461

[22] Filed: Jan. 10, 1994

Related U.S. Application Data

[63] Continuation-in-part of Ser. No. 36,615, Mar. 24, 1993, abandoned.

[51] Int. Cl.$^6$ .............. A61K 31/505; A61K 33/24; C07D 471/04; C07F 7/22
[52] U.S. Cl. .............. 514/258; 514/186; 544/225; 544/279; 544/319; 544/329; 544/334
[58] Field of Search .............. 544/279, 225; 514/258, 186

[56] References Cited

U.S. PATENT DOCUMENTS

| | | | |
|---|---|---|---|
| 5,149,699 | 9/1992 | Ellingboe | 514/258 |
| 5,281,602 | 1/1994 | Newman | 514/258 |
| 5,296,480 | 3/1994 | Newman | 514/258 |

FOREIGN PATENT DOCUMENTS

| | | |
|---|---|---|
| 481614 | 9/1991 | European Pat. Off. |
| 516392 | 5/1992 | European Pat. Off. |
| 500297 | 8/1992 | European Pat. Off. |

Primary Examiner—Emily Bernhardt
Attorney, Agent, or Firm—Arthur G. Seifert

[57] ABSTRACT

This invention relates to substituted pyridopyrimidinones of general formula (I):

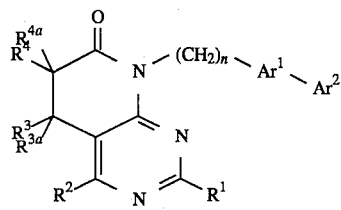

wherein $R^1$ and $R^2$ are independently H, lower alkyl containing 1 to 6 carbon atoms, hydroxyalkyl containing 1 to 6 carbon atoms, formyl, carbonylalkyl containing 1 to 6 carbon atoms, carboxy, or carboxyalkyl containing 1 to 6 carbon atoms; $R^3$ and $R^4$ are independently H, lower alkyl containing 1 to 6 carbon atoms, hydroxy; $R^{3a}$ and $R^{4a}$ are H, and when taken together with $R^3$ and $R^4$ respectively comprise a carbonyl; with the proviso that at least one of the groups R1 and $R^2$ must be hydroxyalkyl, formyl, carbonylalkyl containing 1 to 6 carbon atoms, carboxy, or carboxyalkyl containing 1 to 6 carbon atoms; or $R^3$ and $R^4$ must be hydroxy or taken together with $R^{3a}$ and $R^{4a}$ respectively must comprise a carbonyl; n is 0 to 3; $Ar^1$ is

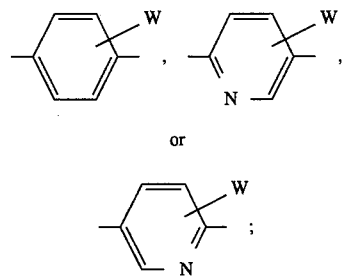

wherein W is H, lower alkyl containing 1 to 6 carbon atoms, halogen, hydroxy, or lower alkoxy containing 1 to 6 carbon atoms; $Ar^2$ is

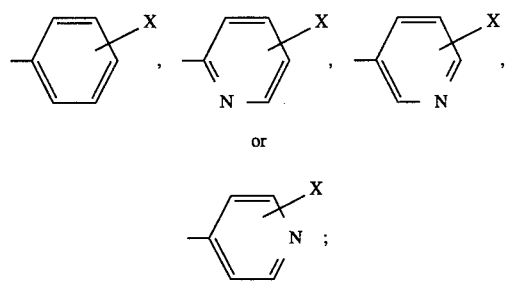

wherein X is $CO_2H$, CN, or

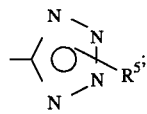

wherein $R^5$ is H, $CH_3$, tert-butyl, tri-n-butylstannyl, or triphenylmethyl; and the pharmaceutically acceptable salts thereof useful for treating hypertension and congestive heart failure, to pharmaceutical compositions, and to methods for production thereof.

15 Claims, No Drawings

SUBSTITUTED PYRIDOPYRIMIDINES AND ANTIHYPERTENSIVES

This application is a continuation-in-part of U.S. patent application Ser. No. 08/036,615 filed Mar. 24, 1993(abandoned).

BACKGROUND OF THE INVENTION

This invention relates to substituted pyridopyrimidines which are useful for the treatment of hypertension and congestive heart failure.

These compounds achieve their hemodynamic effects by antagonizing the effects of angiotensin II; the active component of the renin angiotensin system. Angiotensinogen is converted to angiotensin I by the action of the enzyme renin. Angiotensin II (A II) is formed by angiotensin converting enzyme (ACE) acting on angiotensin I. A II is a powerful vasoconstrictor and is implicated as the cause of high blood pressure in a number of species including man. A II elicits these vasopressor responses by acting at specific receptor sites. The compounds described in this invention compete with A II for these receptor sites, thus antagonizing the vasopressor effects of A II.

R. S. Boger, in U.S. Pat. No. 5,104,877, and K. Atwal, in EP 481448 A, describe methylbiphenyl substituted 4-aminopyrimidines. C. Hoornaert, et al. disclose methylbiphenyl 4-pyrimidinone derivatives in EP 500409 A. A. M. Venkatesan, et al. disclose methylbiphenyl substituted quinazolinones in EP 497150 A. A. H. Ratcliffe, et al. disclose methylbiphenyl substituted naphthyridines in EP 516392 A2. E. Allen, et al. describe substituted pyridopyrimidinones in EP 481614 A. J. W. Ellingboe, et al. describe methylbiphenyl substituted pyridopyrimidines in U.S. Pat. No. 5,149,699. All of the above are claimed as A II antagonists.

The compounds of this invention differ from the above mentioned prior art, except for the last reference, in that they contain a pyrimidine ring fused to a pyridinone ring, with a methylbiphenyl group attached to the pyridinone ring. The compounds described by E. Allen, et al. in EP 481614 A contain a pyrimidinone ring fused to a pyridine ring, and the methylbiphenyl group is attached to the pyrimidinone ring. The compounds of the present invention differ from those described by J. W. Ellingboe, et al. in U.S. Pat. No. 5,149,699 in that they contain at least one hydroxy, hydroxyalkyl, aldehyde, ketone, or carboxy group on the pyridopyrimidinone ring system.

DESCRIPTION OF THE INVENTION

This invention relates to substituted pyridopyrimidinones of general formula (I):

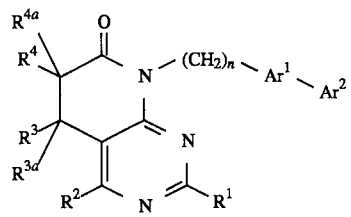

wherein $R^1$ and $R^2$ are independently H, lower alkyl containing 1 to 6 carbon atoms, hydroxyalkyl containing 1 to 6 carbon atoms, formyl, carbonylalkyl containing 1 to 6 carbon atoms, carboxy, or carboxyalkyl containing 1 to 6 carbon atoms; $R^3$ and $R^4$ are independently H, lower alkyl containing 1 to 6 carbon atoms, hydroxy; $R^{3a}$ and $R^{4a}$ are H, and when taken together with $R^3$ and $R^4$ respectively comprise a carbonyl; with the proviso that at least one of the groups R1 and $R^2$ must be hydroxyalkyl, formyl, carbonylalkyl containing 1 to 6 carbon atoms, carboxy, or carboxyalkyl containing 1 to 6 carbon atoms; or $R^3$ and $R^4$ must be hydroxy or taken together with $R^{3a}$ and $R^{4a}$ respectively must comprise a carbonyl; n is 0 to 3; $Ar^1$ is

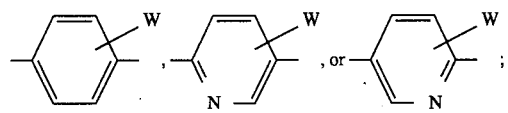

wherein W is H, lower alkyl containing 1 to 6 carbon atoms, halogen, hydroxy, or lower alkoxy containing 1 to 6 carbon atoms; $Ar^2$ is

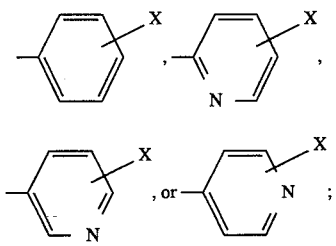

wherein X is $CO_2H$, CN, or

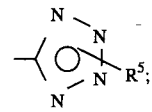

wherein $R^5$ is H, $CH_3$, tert-butyl, tri-n-butylstannyl, or triphenylmethyl; and the pharmaceutically acceptable salts thereof.

A more preferred aspect of the present invention is represented by general formula (II):

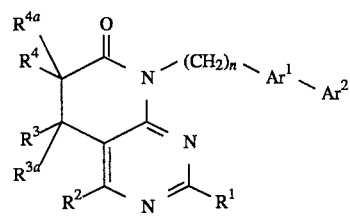

wherein $R^1$ and $R^2$ are independently H, methyl, ethyl, propyl, isopropyl, hydroxymethyl, 1-hydroxyethyl, 1-hydroxypropyl, 1-hydroxybutyl, 1-hydroxyisobutyl, formyl, carbonylmethyl, carbonylethyl, carbonylpropyl, carbonylbutyl, carboxy, or carboxymethyl, carboxyethyl, carboxypropyl, carboxybutyl; $R^3$ and $R^4$ are independently H, methyl, ethyl, propyl, hydroxy; $R^{3a}$ and $R^{4a}$ are H, and when taken together with $R^3$ and $R^4$ respectively comprise a carbonyl; with the proviso that at least one of the groups $R^1$ and $R^2$ must be hydroxyalkyl, formyl, carbonylalkyl containing 1 to 6 carbon atoms, carboxy, or carboxyalkyl containing 1 to 6 carbon atoms; or $R^3$ and $R^4$ must be hydroxy, or taken together with $R^{3a}$ and $R^{4a}$ respectively must comprise a carbonyl; n is 1; $Ar^1$ is

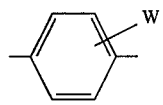

wherein W is H, lower alkyl containing 1 to 6 carbon atoms, halogen, hydroxy, or lower alkoxy containing 1 to 6 carbon atoms; Ar² is

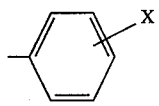

wherein X is CO₂H, or

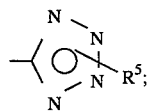

wherein $R^5$ is H, $CH_3$, tert-butyl, tri-n-butylstannyl, or triphenylmethyl; and the pharmaceutically acceptable salts thereof.

A still more preferred aspect of the present invention is represented by general formula (III):

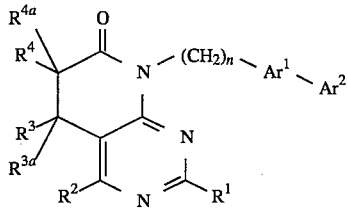

III wherein $R^1$ and $R^2$ are independently H, methyl, hydroxymethyl, formyl; $R^3$ and $R^4$ are independently H, hydroxy; $R^{3a}$ and $R^{4a}$ are H, and when taken together with $R^3$ and $R^4$ respectively comprise a carbonyl; with the proviso that at least one of the groups R1 and $R^2$ must be hydroxymethyl or formyl; or $R^3$ and $R^4$ must be hydroxy, or taken together with $R^{3a}$ and $R^{4a}$ respectively must comprise a carbonyl; n is 1; $Ar^1$ is

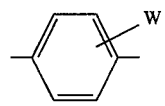

wherein W is H; Ar² is

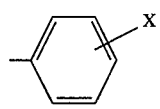

wherein X is

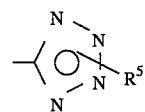

wherein $R^5$ is H, $CH_3$, tert-butyl, or triphenylmethyl; and the pharmaceutically acceptable salts thereof.

The compounds of the present invention wherein $R^1$ or $R^2$ contain a carbonyl group or wherein $R^3$ or $R^4$ taken together $R^{3a}$ or $R^{4a}$ respectively comprise a carbonyl group can exist in more than one tautomeric form. All such tautomers are included in the present invention.

This invention also includes mixtures of optically active isomers or partially or completely resolved isomers of the compounds disclosed.

The most preferred aspects of the present invention are:

2-methyl-7-oxo-8-[2 '-(1H-tetrazol-5-yl)biphenyl-4-ylmethyl]- 5,6,7,8tetrahydropyrido[2,3-d]pyrimidine-4-carbaldehyde and the pharmaceutically acceptable salts thereof;

2-hydroxymethyl-4-methyl-8-[2'-(1H-tetrazol-5-yl)biphenyl-4-ylmethyl]- 5,8-dihydro-6H-pyrido[2,3-d]pyrimidin-7-one and the pharmaceutically acceptable salts thereof;

4-hydroxymethyl-2-methyl-8-[2'-(1H-tetrazol-5-yl)biphenyl-4-ylmethyl]- 5,8-dihydro-6H-pyrido[2,3-d]pyrimidin-7-one and the pharmaceutically acceptable salts thereof;

2,4-dimethyl-5-hydroxy-8-[2'-(1H-tetrazol-5-yl)biphenyl-4-ylmethyl]-8H-pyrido[2,3-d]pyrimidin-7-one and the pharmaceutically acceptable salts thereof;

2,4-dimethyl-5-hydroxy-8-[2'-(1H-tetrazol-5-yl)biphenyl-4-ylmethyl]- 6,8-dihydro-5H-pyrido[2,3-d]pyrimidin-7-one and the pharmaceutically acceptable salts thereof;

2,4-dimethyl-6-hydroxy-8- [2'-(1H-tetrazol-5-yl)biphenyl-4-ylmethyl]- 5,8-dihydro-6H-pyrido[2,3-d]pyrimidin-7-one and the pharmaceutically acceptable salts thereof.

Further, 2,4-Dimethyl-5-hydroxy-8-[2'-(1H-tetrazol-5-yl)biphenyl- 4-ylmethyl]-8H-pyrido[2,3-d]pyrimidin-7-one (Example 4) and 5-Hydroxy- 2,4-dimethyl-[2'-(1H-tetrazol-5-yl )-biphenyl-4-ylmethyl]-6,8-dihydro-5H-pyrido[ 2,3-d] pyrimidine-7-one (Example 6) have been identified in studies conducted in rats as significant metabolites of the compound of Example 3 of the aforementioned U.S. Pat. No. 5,149,599, the former being present significantly longer and in greater amounts than the latter. However, in similar metabolic studies in dogs, no significant metabolites were found.

PROCESS

The compounds of the present invention are prepared according to the general sequences of reactions outlined below:

Scheme I

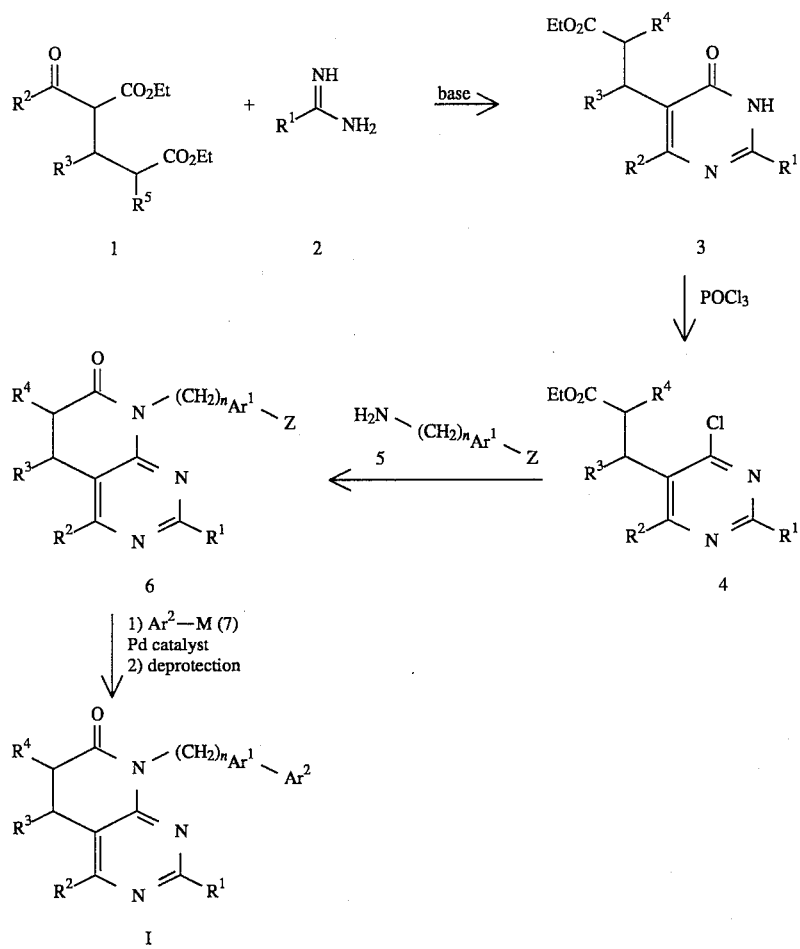

$R^1$, $R^2$, $R^3$, $R^4$, $R^{3a}$, $R^{4a}$, n, $Ar^1$, and $Ar^2$ are as defined above; Z is chloro, bromo, iodo, or trifluoromethanesulfonate; and M is a boronic acid or trialkyltin.

As illustrated in Scheme I, β-keto ester 1 is condensed with amidine 2 in the presence of a base such as sodium ethoxide in an alcoholic solvent such as ethanol at temperatures ranging from ambient to reflux to yield pyrimidinone 3. Treatment of pyrimidinone 3 with phosphorus oxychloride under reflux gives chloropyrimidine 4. The reaction of 4 with amine 5 in the presence of an organic base such as triethylamine or an inorganic base such as potassium carbonate in a polar solvent such as ethanol, butanol, or dimethylsulfoxide at temperatures ranging from ambient to reflux yields pyridopyrimidine 6. The reaction of 6 with an arylboronic acid or aryltrialkyltin 7 in the presence of a palladium catalyst in a solvent such as dimethylformamide or toluene yields, after cleavage of protecting groups, pyridopyrimidine I. In the case where the substituent (X) on $Ar^2$ is a nitrile, it can be converted to a tetrazole under standard conditions utilizing an azide reagent.

Scheme II

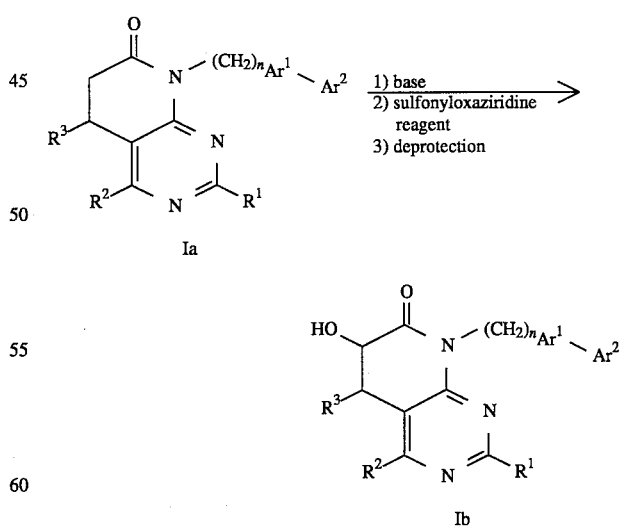

$R^1$, $R^2$, $R^3$, n, $Ar^1$, and $Ar^2$ are as defined above.

An oxygen substituent can be introduced at the 6-position according to the reactions illustrated in Scheme II. Thus, pyridopyrimidine Ia with a protecting group on the carboxylic acid or tetrazole moiety of $Ar^2$ is treated with a base such as lithium diisopropylamide or sodium hexamethyldisilazide in an aprotic solvent such as tetrahydrofuran or dimethoxyethane at low temperatures (−78° C. to 0° C.) and then a sulfonyloxaziridine reagent such as phenylsulfonyloxaziridine. Deprotection of the tetrazole or carboxylic acid group on $Ar^2$ with acid or base yields pyridopyrimidine Ib.

ing from ambient to reflux yields pyrimidine 11. The reaction of 11 with amine 5 in the presence of an organic base such as triethylamine or an inorganic base such as potassium carbonate in a polar solvent such as ethanol, butanol, or dimethylsulfoxide at temperatures ranging from ambient to reflux, and hydrolysis of the enol with aqueous acid yields 5-ketopyrimidine 12. The reaction of 12 with an arylboronic

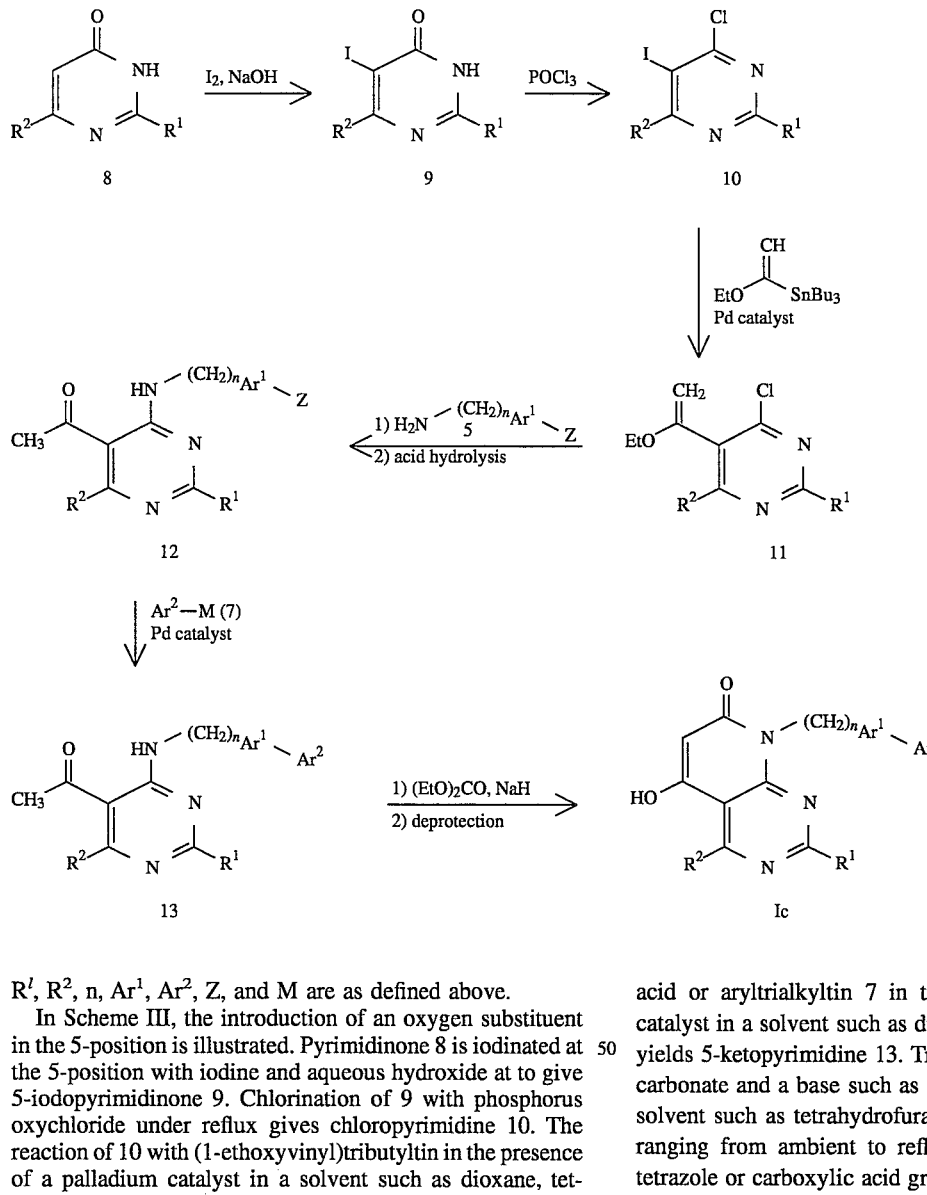

Scheme III $R^1$, $R^2$, n, $Ar^1$, $Ar^2$, Z, and M are as defined above.

In Scheme III, the introduction of an oxygen substituent in the 5-position is illustrated. Pyrimidinone 8 is iodinated at the 5-position with iodine and aqueous hydroxide at to give 5-iodopyrimidinone 9. Chlorination of 9 with phosphorus oxychloride under reflux gives chloropyrimidine 10. The reaction of 10 with (1-ethoxyvinyl)tributyltin in the presence of a palladium catalyst in a solvent such as dioxane, tetrahydrofuran, or dimethylformamide at temperatures rangacid or aryltrialkyltin 7 in the presence of a palladium catalyst in a solvent such as dimethylformamide or toluene yields 5-ketopyrimidine 13. Treatment of 13 with a dialkyl carbonate and a base such as sodium hydride in an aprotic solvent such as tetrahydrofuran or toluene at temperatures ranging from ambient to reflux, and deprotection of the tetrazole or carboxylic acid group on $Ar^2$ with acid or base yields pyridopyrimidine Ic.

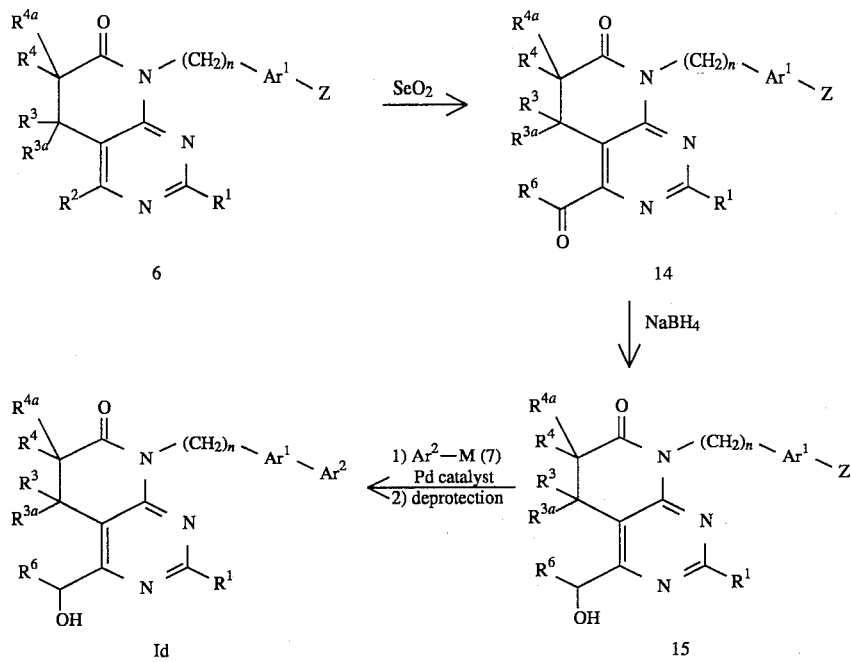

Scheme IV wherein $R^1$, $R^2$, $R^3$, $R^4$, $R^{3a}$, $R^{4a}$, n, $Ar^1$, $Ar^2$, Z, and M are as defined above, and $R^6$ is H or lower alkyl containing 1 to 5 carbon atoms.

As shown in Scheme IV, an oxygen substituent can be introduced on the $R^2$ group by an oxidative process. Thus, intermediate pyridopyrimidine 6 is treated with an oxidizing reagent such as selenium dioxide in an organic solvent such as dioxane or pyridine at temperatures ranging from ambient to reflux to yield pyridopyrimidine 14. The carbonyl group is reduced to a hydroxy group with sodium borohydride in an alcoholic solvent such as ethanol or isopropanol to give pyridopyrimidine 15. The reaction of 15 with an arylboronic acid or aryltrialkyltin 7 in the presence of a palladium catalyst in a solvent such as dimethylformamide or toluene yields, after cleavage of protecting groups, pyridopyrimidine Id. Pyridopyrimidine I can also be oxidized directly with an oxidizing reagent such as selenium dioxide. Other oxidizing agents, such as potassium permanganate can be used to introduce a hydroxy group at the 6-position to give a pyridopyrimidine I wherein $R^3$ or $R^{3a}$ is a hydroxy group.

The compounds of this invention may also form salts with inorganic or organic bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The present invention also provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carder.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, β-blocking agents or ACE inhibitors.

The present invention further provides a compound of the invention for use as an active therapeutic substance. Compounds described in this invention are of particular use in the treatment of hypertension. They can also be used for the treatment of congestive hem-failure.

The present invention further provides a method of treating hypertension in mammals including man, which comprises administering to the afflicted mammal an antihypertensive effective amount of a compound or a pharmaceutical composition of the invention.

PHARMACOLOGY

The high affinity of the compounds for the angiotensin II receptor was established using a rat adrenal receptor binding assay, measuring the displacement of radiolabeled angiotensin II from the receptor, described as follows: Anesthetize male Sprague-Dawley rats (300–400 g body weight) with $CO_2$ and sacrifice by cervical dislocation. Dissect adrenal glands and keep in ice-cold sucrose buffer (0.2M sucrose, 1 mM EDTA, 10 mM Trizma base, pH=7.2). Remove medulla by squashing. Mince the cortex, rinse and homogenize in a chilled ground glass tissue grinder with 15 mL sucrose buffer. Centrifuge at 3000× g for 10 min. (Sorvall RCSC centrifuge, SS34 rotor 6200 rpm). Decant supernatant through gauze. Centrifuge combined supernatants at 12000× g for 13 min. (Beckman ultracentrifuge, 80Ti rotor, 13000 rpm). Centrifuge the supernatant from the previous step at 102000×g for 60 min. (Beckman ultracentrifuge, 80Ti rotor, 38200 rpm). All steps are carried out at 4° C. Resuspend the pellet in 0.5 mL assay buffer (50 mM Tris HCl, 5 mM $MgCl_2$, 0.2% BSA (protease-free), pH=7.4, 25° C.). Store on ice. Determine membrane protein by Lowry or Bradford assay with BSA as standard. The binding assay is performed in triplicate, in 12×75 mm plastic test tubes or in a 96-well plate (final volume of 0.25 mL). Add 140 μL assay buffer. Add 10 μL cold A II (to give final concentrations of $10^{-10}$–$10^{-7}$M for standard curve and $10^{-4}$M for nonspecific binding), compounds (e.g., for final concentrations of 25 and 100 μM or 1 μM, 10 nM and 100 nM) in 50% DMSO, or 50% DMSO as a control. Add 50 μL membrane suspension (e.g., 10 μg protein). Preincubate for 30 min at 25° C. Add 50 μL $^{125}$I-A II which has been prepared as shown below (final concentration =1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes 3X with 5 mL cold buffer (assay buffer without BSA). Cut and deposit the filter discs into test tubes and count on gamma counter for 1 min. Adjust the specific activity of $^{125}$I-A II purchased from New England Nuclear to 500 μCi/nmole by adding cold A II in water. Calculate the quantities of hot A II and the cold A II needed and make the dilution. Aliquot, seal tight, and store frozen until needed. Calculate the concentration of the total A II (hot +cold) after dilution. On the day of assay, thaw the frozen aliquot and adjust the volume to give a concentration of 5 pmole/mL (or 0.25 pmole/50 μL) with assay buffer (+protease-free BSA). For final concentration of 1 nM $^{125}$I-A II in the assay, add 50 μL (or 0.25 pmole) per test tube to a final volume of 250 μL. The results of these binding assays are reported as the inhibitory concentration of the test compound necessary to achieve fifty percent displacement of radiolabeled angiotensin II from its receptor ($IC_{50}$), or the percent displacement of binding of A II at its receptor at $10^{-8}$M concentration of test compound (% I). All the examples cited in this invention displayed significant inhibition of A II binding in this assay. Typically these compounds displayed an $IC_{50}$ in this assay of less than or equal to 50 μM.

In accordance with their ability to antagonize angiotensin II, the compounds of this invention show antihypertensive action in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 μg/kg/min (at 9.6 μL/min). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the product of Example 2 administered at 3 mg/kg id lowered the A II dependent blood pressure by an average of 30% four hours post-administration.

In further accordance with their ability to antagonize angiotensin II, the compounds of this invention show anti hypertensive action in the following Goldblatt (2K-1C) hypertensive rat model. Sprague-Dawley rats weighing 150 g were anesthetized with pentobarbital (50 mg/kg ip) and the left renal artery was clipped with a silver wire bent to an internal diameter of 0.2 mm. The hypertension was established 4–7 weeks after clipping. At that time, the animals were anesthetized with pentobarbital (50 mg/kg ip) and the right carotid artery was cannulated. The catheter was passed subcutaneously to the dorsal side of the neck and exteriorized. The animals were fasted overnight but allowed access to water and the experiment was performed the next morning. The carotid catheter was connected to a blood pressure transducer which was linked to a $MI^2$ computer data acquisition system or to a Grass or Beckman recorder for the recording of mean arterial pressure (MAP) and heart rate. For oral administration, the rats were given either a compound of the invention (1, 3 or 10 mg/kg), losartan (30 mg/kg) as a standard or vehicle (0.5% methyl cellulose in distilled water) by gastric gavage (ig) in a volume of 5 mL/kg. For intravenous administration, the rats were given either a compound of the invention (0.03, 0.1, 1, 3 or 10 mg/kg) or vehicle ($\leq$50% $NaHCO_3$ in distilled water) in a volume of 1 mL/kg. In all experiments, saline was infused into the arterial cannula at 5 μL/min throughout the experiment to maintain patency of the cannula. Each compound was administered to a separate group of 6–12 rats and MAP and heart rate were recorded for 24 h. Data was recorded every 15 min for the first h, every 30 min for the second h, hourly up to 8 h, and then at 22, 23, and 24 h following dosing. At each time point following dosing, averages were determined for absolute MAP, change in MAP (in mm Hg), and heart rate for all animals, and the standard error of the mean was calculated. For example, the product of Example 4, administered at 10 mg/kg ig, showed a maximum decrease in MAP of 66 mm Hg 23 hours post-administration. The product of Example 4, administered at 0.1 mg/kg iv, showed a maximum decrease in MAP of 67 mm Hg 4 hours post-administration. The product of Example 6, administered ig at 10 mg/kg, showed a maximum decrease in MAP of 71 mm Hg 9 hours post-administration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of restenosis, left ventricular dysfunction, diabetic retinopathy, Alzheimers disease, in the enhancement of cognition, in treatment of elevated intraoccular pressure, and in the enhancement of retinal blood flow. The application of the compounds of this invention for these and similar disorders will be apparent to those skilled in the art.

Specific procedures are described in the following examples. These examples are given to illustrate the invention and should not be construed as limiting the invention set forth in the appended claims.

EXAMPLES

Example 1

2-Methyl-7-oxo-8-[2'-(1H-tetrazol-5-yl)biphenyl-4-ylmethyl]-5,6,7,8-tetrahydropyrido[2,3-d]pyrimidine-4-carbaldehyde A mixture of 2,4-dimethyl-8-[2'-(1H-tetrazol-5-yl)biphenyl-4-ylmethyl]- 5,8-dihydro-6H-pyrido[2,3-d]pyrimidin-7-one (822 mg, 2.00 mmol) (prepared according to J. W. Ellingboe, et al. U.S. Pat. No. 5,149,699), selenium dioxide (222 mg, 2.00 mmol), and dioxane (10 mL) was heated under reflux for 6 h. Additional selenium dioxide (222 mg, 2.00 mmol) was added and heating was continued for 18 h. The mixture was filtered and the filtrate was concentrated. Purification by flash chromatography (10% MeOH/CH$_2$Cl$_2$) gave 316 mg of a yellow foam. The foam was triturated with acetone and the filtrate was cooled in a freezer to give 102 mg (12%) of product as an off-white solid, mp 246°–247° C.

$^1$H NMR (DMSO-d$_6$) δ2.47 (s, 3 H), 2.74 (t, J=7.1 Hz, 2H), 2.90 (t, J=7.1 Hz, 2H), 5.18 (s, 2H), 7.00 (d, J=8.3 Hz, 2H), 7.20 (d, J= 8.3 Hz, 2H), 7.54 (m, 2H), 7.64 (m, 2H), 8.38 (s, 1H).

IR (KBr, cm$^{-1}$)1710.

Anal. calcd for C$_{23}$H$_{19}$N$_7$O$_2$: C, 64.93; H, 4.50; N, 23.05; Found: C, 65.00; H, 4.90; N, 23.41.

Example 2

2-Hydroxymethyl-4-methyl-8-[2'-(1H-tetrazol-5-yl)biphenyl-4-ylmethyl]-5,8-dihydro-6H-pyrido[2,3-d]pyrimidin-7 -one Step 1

Ethyl 3-(6-Methyl-2-methoxymethyl-3H-pyrimidin-4-on-5-yl)propionate

A mixture of NaOEt (0.088 mol) in EtOH (prepared from 2.0 g of Na and 70 mL of EtOH), methoxyacetamidine hydrochloride (5.4 g, 0.044 mol), and diethyl acetylglutarate (10.0 g, 0.044 mol) was heated under reflux for 24 h. The mixture was concentrated, taken up in water, acidified to pH 4 with conc. HCl, and extracted with CH$_2$Cl$_2$. The extracts were washed with brine, dried (MgSO$_4$), and concentrated. Trituration with ether gave 4.6 g (42%) of product as an off-white solid, mp 87°–90° C.

$^1$H NMR (DMSO-d$_6$) δ1.15 (t, J=7.2 Hz, 3H), 2.22 (s, 3H), 2.45 (s, 3H), 2.63 (t, J=7.8 Hz, 2H), 3.30 (s, 3H), 4.08 (q, J=7.2 Hz, 2H), 4.18 (s, 2H), 12.40 (br s, 1H).

Step 2

Ethyl 3-(4-Chloro-6-methyl-2-methoxymethylpyrimidin-5-yl)propionate

A mixture of ethyl 3-(6-methyl-2-methoxymethyl-3H-pyrimidin-4-on- 5yl)propionate (4.00 g, 15.6 mmol) and phosphorus oxychloride (25 mL) was heated under reflux for 2 h. The mixture was concentrated, cooled, and poured onto ice. 1N NaOH was added to bring the pH to 6 and the mixture was extracted with EtOAc. The extracts were dried (MgSO$_4$) and concentrated to give 3.6 g (84%) of product as a brown oil.

$^1$H NMR (DMSO-d$_6$) δ1.18 (t, J=7.0 Hz, 3H), 2.60 (s, 3H), 3.01 (t, J=8.1 Hz, 2H), 3.36 (s, 3H), 3.36 (s, 3H), 4.05 (q, J=7.0 Hz, 2H), 4.48 (s, 2H).

Step 3

8-[(4-Bromophenyl)methyl]-4-methyl-2-methoxymethyl-5,8-dihydro-6H-pyrido[2,3-d]pyrimidin-7-one A mixture of ethyl 3-(4-chloro-6-methyl-2-methoxymethylpyrimidin-5-yl)propionate (3.6 g, 0.013 mol), 4-bromobenzylamine hydrochloride (3.0 g, 0.013 mol), NaHCO$_3$ (2.4 g, 0.028 mol), and nBuOH (25 mL) was heated under reflux for 24 h. The mixture was concentrated, taken up in water, and extracted with CH$_2$Cl$_2$. The combined extracts were dried (MgSO$_4$) and concentrated to give a brown oil. Purification by flash chromatography (5% MeOH/CH$_2$Cl$_2$) gave 3.6 g (72%) of product as an off-white solid, mp 64°–66° C.

$^1$H NMR (DMSO-d$_6$) δ2.40 (s, 3H), 2.77 (t, J=7.9 Hz, 2H), 2.91 (t, J=7.9 Hz, 2H), 3.26 (s, 3H), 4.38 (s, 2H), 5.15 (s, 2H), 7.26 (d, J= 8.3 Hz 2H), 7.46 (d, J=8.3 Hz, 2H).

Anal. calcd for C$_{17}$H$_{18}$BrN$_3$O$_2$: C, 54.27; H, 4.82; N, 11.17; Found: C, 54.31; H, 4.76; N, 11.03.

Step 4

8-[(4-Bromophenyl)methyl]-2-hydroxymethyl-4-methyl-5,8-dihydro-6H-pyrido[2,3-d]pyrimidin-7-one To a solution of 8-[(4-bromophenyl)methyl]-6-methyl-2-methoxymethyl- 5,8-dihydro-6H-pyrido[2,3-d]pyrimidin-7-one (1.00 g, 2.70 mmol) and pyridine (0.11 g, 1.30 mmol) in CHCl$_3$ (9 mL) was added iodotrimethylsilane (0.77 g, 3.80 mmol). The mixture was heated under reflux for 30 h and MeOH (0.5 mL) was added. The mixture was concentrated, taken up in CH$_2$Cl$_2$, washed with aqueous Na$_2$SO$_3$ and brine, dried (MgSO$_4$), and concentrated. Purification by flash chromatography (5% MeOH/CH$_2$Cl$_2$) gave o.54 g (56%) of product as a colorless foam.

$^1$H NMR (DMSO-d$_6$) δ2.40 (s, 3H), 2.73 (t, J=7.6 Hz, 2H), 2.87 (t, J=7.6 Hz, 2H), 4.43 (d, J=6.2 Hz, 2H), 5.09 (t, J=6.2 Hz, 1H), 5.19 (s, 2H), 7.27 (d, J=8.2 Hz, 2H), 7.43 (d, J=8.2 Hz, 2H).

Step 5

2-Hydroxymethyl-4-methyl-8-[2'-(1 -tert-butyl-1H-tetrazol-5-yl)biphenyl- 4-ylmethyl]-5,8-dihydro-6H-pyrido[2,3-d]pyrimidin-7-one A mixture of 8-[(4-bromophenyl)methyl]-2-hydroxymethyl-6-methyl- 5,8-dihydro-6H-pyrido[2,3-d]pyrimidin-7-one (0.95 g, 2.62 mmol), 2-[( 1-tert-butyl)-1H-tetrazol-5-yl] phenylboronic acid (0.72 g, 2.90 mmol) (prepared according to J. W. Ellingboe, et al. U.S. Pat. No. 5,149,699), 2M Na$_2$CO$_3$ (5.5 mL), tetrakis(triphenylphosphine)palladium(0) (100 tug, 0.086 mmol), EtOH (3 mL)and toluene (16 mL) was heated under reflux for 20 h. The mixture was diluted with CH$_2$Cl$_2$ and the layers were separated. The organic phase was dried (MgSO$_4$) and concentrated to give an orange oil. Purification by flash chromatography (4% MeOH/CH$_2$Cl$_2$) gave 1.20 g (90%) of product as a colorless foam.

$^1$H NMR (DMSO-d$_6$) δ1.42 (s, 9H), 2.41 (s, 3H), 2.72 (t, J=7.3 Hz, 2 H), 2.89 (t, J=7.3 Hz, 2H), 4.44 (d, J=6.0 Hz,

2H), 5.08 (t, J=6.0 Hz, 1H), 5.23 (s, 2H), 6.98 (d, J=7.4 Hz, 2H), 7.23 (d, J=7.4 Hz, 2H), 7.54 (m, 3H), 7.78 (d, J=7.5 Hz, 1H).

Step 6

2-Hydroxymethyl-4-methyl-8-[2'-(1H-tetrazol-5-yl)biphenyl-4-ylmethyl]- 5,8dihydro-6H-pyrido[2,3-d]pyrimidin-7-one A mixture of 2-hydroxymethyl-4-methyl-8-[2'-(1-tert-butyl-1H-tetrazol- 5-yl)biphenyl-4-ylmethyl]-5,8-dihydro-6H-pyrido[2,3-d]pyrimidin-7-one (1.2 g, 2.50 mmol), methanesulfonic acid (2.40 g, 25.0 mmol), and toluene (14 mL) was heated under reflux for 20 h. The mixture was concentrated, taken up in water, and the pH was adjusted to 7–8 with 1 N NaOH. The aqueous mixture was extracted with EtOAc (discarded), acidified to pH 4 with 1N HCl, and extracted with $CHCl_3$. The $CHCl_3$ layers were dried ($MgSO_4$) and concentrated to give 1.10 g of a foam. Trituration with EtOAc/acetone and recrystallization from EtOH gave 0.45 g (46%) of product as a white solid, mp 218°–220° C.

$^1$H NMR (DMSO-$d_6$) δ2.41 (s, 3H), 2.74 (t, J=7.0 Hz, 2H), 2.91 (t, J=7.0 Hz, 2H), 4.43 (s, 2H), 5.15 (br s, 1H), 5.24 (s, 2H), 7.00 (d, J= 8.0 Hz, 2H), 7.23 (d, J=8.0 Hz, 2H), 7.57 (m, 4H).

Anal. calcd for $C_{23}H_{21}N_7O_2$: C, 64.43; H, 4.95; N, 22.94; Found: C, 64.73; h, 5.15; N, 22.55.

Example 3

4-Hydroxymethyl-2-methyl-8-[2'-(1H-tetrazol-5-yl) biphenyl-4-ylmethyl]- 5,8-dihydro-6H-pyrido[2,3-d]pyrimidin-7-one Step 1

8-[(4-Bromophenyl)methyl]-2-methyl-7-oxo-5,6,7,8-tetrahydropyrido[ 2,3-d]pyrimidine-4-carbaldehyde A mixture of 8-[(4-bromophenyl)methyl]-2,4-dimethyl-5,8-dihydro-6H-pyrido[2,3-d]pyrimidin-7-one (692 mg, 2.00 mmol) (prepared according to the procedures described in Steps 1–3 of Example 2), selenium dioxide (244 mg, 2.20 mmol) and dioxane (10 mL) was heated under reflux for 17 h. The mixture was filtered and the filtrate was concentrated. Purification by flash chromatography (30% EtOAc/hexane) gave 576 mg (80%) of product as a yellow solid, mp 124°–126° C.

$^1$H NMR (CDCl$_3$) δ2.70 (s, 3H), 2.73 (t, J=7.6 Hz, 2H), 3.37 (t, J=7.6 Hz, 2H), 5.27 (s, 2H), 7.31 (d, J=8.5 Hz, 2H), 7.39 (d, J=8.5 Hz, 2H), 10.02 (s, 1H).

IR (KBr, cm$^{-1}$) 1710, 1695.

Anal. calcd for $C_{16}H_{14}BrN_3O_2$: C, 53.35; H, 3.92; N, 11.66; Found: C, 53.16; H, 3.78; N, 11.51.

Step 2

8-[(4-Bromophenyl)methyl]4-hydroxymethyl-2-methyl-5,8-dihydro- 6H-pyrido[2,3-d]pyrimidin-7-one To a solution of 8-[(4-bromophenyl)methyl]-2-methyl-7-oxo-5,6,7,8-tetrahydropyrido[2,3-d]pyrimidine-4-carbaldehyde (550 mg, 1.53 mmol) in tetrahydrofuran (5 mL) and isopropanol (2 mL) was added sodium borohydride (116 mg, 3.05 mmol). After 45 min, the mixture was cooled to 0° C. and $CO_2$ was bubbled in for 5 min. The mixture was filtered and the filtrate was concentrated to give 677 mg of a yellow foam. Purification by flash chromatography (5% MeOH/ $CH_2Cl_2$) gave 496 mg (90%) of product as an off-white solid, mp 159°–160° C.

$^1$H NMR (CDCl$_3$) δ8 2.65 (s, 3H), 2.75 (s, 4H), 4.40 (br s, 1H), 4.63 (s, 2H), 5.26 (s, 2H), 7.31 (d, J=8.3 Hz, 2H), 7.39 (d, J=8.3 Hz, 2H).

Anal. calcd for $C_{16}H_{16}BrN_3O_2$: C, 53.05; H, 4.45; N, 11.60; Found: C, 52.60; H, 4.37; N, 11.47.

Step 3

4-Hydroxymethyl-2-methyl-8-[2'-(1 -tert-butyl-1H-tetrazol-5-yl)biphenyl- 4ylmethyl]-5,8-dihydro-6H-pyrido[2,3-d]pyrimidin-7-one A mixture of 8-[(4-bromophenyl)methyl]-4-hydroxymethyl-2-methyl-5,8-dihydro-6H-pyrido[2,3-d]pyrimidin-7-one (490 mg, 1.35 mmol), 2-[(1-tert-butyl)-1H-tetrazol-5-yl]phenylboronic acid (367 mg, 1.49 mmol) (prepared according to J. W. Ellingboe, et al. U.S. Pat. No. 5,149,699), $Na_2CO_3$ (287 mg, 2.71 mmol), tetrakis(triphenylphosphine) palladium(0) (78 mg, 0.07 mmol), EtOH (1 mL), water (2 mL), and toluene (6 mL) was heated under reflux for 23 h. The mixture was diluted with EtOAc, washed with saturated aqueous $NaHCO_3$, brine, dried ($MgSO_4$), and concentrated to give a yellow oil. Purification by flash chromatography (5% MeOH/$CH_2Cl_2$) gave 590 mg (90%) of product as an off-white foam. An analytical sample (40 mg) was crystallized from ether/acetone, mp 164°–166° C.

$^1$H NMR (CDCl$_3$) δ1.50 (s, 9H), 2.63 (s, 3H), 2.74 (s, 4H), 4.40 (br s, 1H), 4.63 (s, 2H), 5.31 (s, 2H), 7.06 (d, J=8.2 Hz, 2H), 7.31 (d, J= 8.2 Hz 2H), 7.45 (m, 3H), 7.84 (m, 1H).

Anal. calcd for $C_{27}H_{29}N_7O_2$: C, 67.06; H, 6.04; N, 20.28; Found: C, 66.99; H, 6.07; N, 19.91.

Step 4

4-Hydroxymethyl-2-meth yl-8-[2'-(1H-tetrazol-5-yl)biphenyl-4-ylmethyl]-5,8-dihydro-6H-pyrido[2,3-d]pyrimidin-7-one A mixture of 4-hydroxymethyl-2-methyl-8-[2'-(1-tert-butyl-1H-tetrazol-5-yl)biphenyl-4-ylmethyl]-5,8-dihydro-6H-pyrido[2,3-d]pyrimidin-7-one (550 mg, 1.14 mmol), methanesulfonic acid (1.10 g, 11.40 mmol), and toluene (10 mL) was heated under reflux for 4 days. The mixture was concentrated, 1N KOH (11.4 mL) was added, and the mixture was extracted with $CHCl_3$ (discarded). The aqueous phase was acidified to pH4–5 with 1N HCl and extracted with $CHCl_3$. The extracts were dried and concentrated to give 94 mg of a yellow foam. Trituration with acetone and recrystallization from EtOH gave 46 mg (9%) of product as a white solid, mp 246°–247° C.

$^1$H NMR (DMSO-$d_6$) δ2.47 (s, 3H), 2.72 (t, J=8.1 Hz, 2H), 2.97 (t, J=8.1 Hz, 2H), 4.51 (s, 2H), 5.20 (s, 2H), 5.26 (br s, 1H), 7.00 (d, J= 8.1 Hz, 2H), 7.20 (d, J=8.1 Hz, 2H), 7.55 (m, 2H), 7.65 (m, 2H).

Anal. calcd for $C_{23}H_{21}N_7O_2$: C, 64.63; H, 4.95; N, 22.94; Found: C, 64.41; H, 4.88; N, 22.20.

Example 4

2,4-Dimethyl- 5-hydroxy-8-[2'-(1H-tetrazol-5-yl)biphenyl-4-ylmethyl]-8H-pyrido [2,3-d]pyrimidin-7-one Sesquihydrate Step 1

2,6-Dimethyl-5-iodo-4-hydroxypyrimidine

A mechanically stirred mixture of 2,6-dimethyl-4-hydroxypyrimidine (50.0 g, 0.403 mol), iodine (102.2 g, 0.403 mol), and 1N NaOH (503 mL) was heated under reflux for 2 h. The mixture was extracted with $CHCl_3$ (some product fell out of solution and was collected by filtration: 24.5 g). The extracts were dried $MgSO_4$) and concentrated to give 40.9 g of an orange solid which contained starting material and product. Trituration with EtOAc gave 26.0 g of product. The total yield of product was 50.5 g (50%), mp 208–210 (dec). An analytical sample was recrystallized from EtOH, mp 216–218.

¹H NMR (DMSO-d₆) δ2.21 (s, 3H), 2.39 (s, 3H), 12.58 (br s, 1H).

Anal. calcd for C₆H₇IN₂O: C, 28.82; H, 2.82; N, 11.20; Found: C, 28.85; H, 2.76; N, 10.98.

Step 2

4-Chloro-2,6-dimethyl-5-iodopyrimidine

A mixture of 2,6-dimethyl-5-iodo-4-hydroxypyrimidine (24.5 g, 0.098 mol), phosphorus oxychloride (30.0 g, 0.196 mol) and toluene (200 mL) was heated under reflux for 1 h. The mixture was concentrated and ice water (100 mL) was added. The pH was adjusted to 5 with 2.5N NaOH and the mixture was extracted with CH₂Cl₂. The combined extracts were washed with brine, dried MgSO₄), and concentrated to give 24.6 g of a brown solid. The crude product was combined with 26.0 g of similarly prepared material and filtered through a short column of silica gel eluted with CH₂Cl₂ to give 33.8 g (62%) of product as a yellow solid. An analytical sample was recrystallized from hexane/ CH₂Cl₂, mp 62°–64° C.

¹H NMR (CDCl₃) δ2.61 (s, 3H), 2.73 (s, 2H).

Anal. calcd for C₆H₆ClIN₂: C, 26.84; H, 2.26; N, 10.44; Found: C, 27.04; H, 2.15; N, 10.14.

Step 3

4-Chloro-2,6-dimethyl-5-(1-ethoxyvinyl)pyrimidine

A mixture of 4-chloro-2,6-dimethyl-5-iodopyrimidine (13.5 g, 0.050 mol), ( 1ethoxyvinyl)tributyltin (20.0 g, 0.055 mol), lithium chloride (6.4 g, 0.150 mol), tetrakis(triphenylphosphine)palladium(0) (1.7 g, 0.0015 mol), and dioxane (100 mL) was heated under reflux for 23 h. Additional tetrakis(triphenylphosphine)palladium(0) (1.1 g, 0.0010 mol) was added and heating was continued for 25 h. The mixture was cooled, diluted with EtOAc, and ! N KF (100 mL) was added. The solids were removed by filtration through Celite and the layers were separated. The organic phase was washed with pH 7 phosphate buffer (100 mL), brine (100 mL), dried MgSO₄), and concentrated. Purification by flash chromatography (twice; 5–10% EtOAc/hexane) gave 6.44 g (61%) of product as a colorless oil.

¹H NMR (CDCl₃) δ1.35 (t, J=7.0 Hz, 3H), 2.49 (s, 3H), 2.65 (s, 3H), 3.91 (q, J=7.0 Hz, 3H), 4.21 (d, J=2.8 Hz, 1H), 4.52 (d, J=2.8 Hz, 1H).

Anal. calcd for C₁₀H₁₃ClN₂O: C, 56.47; H, 6.16; N, 13.17; Found: C, 55.13; H, 5.97; N, 13.16.

Step 4

4-(4-Bromobenzylamino)-2,6-dimethyl-5-(1-ethoxyvinyl)pyrimidine

A mixture of 4-chloro-2,6-dimethyl-5-(1-ethoxyvinyl)pyrimidine (3.00 g, 0.0141 mol), 4-bromobenzylamine hydrochloride (3.45 g, 0.0155 mol), NaHCO₃ (2.37 g, 0.0282 mol), and n-butanol (20 mL) was heated under reflux for 70 h. The mixture was concentrated, taken up in EtOAc, washed with water, dried MgSO₄), and concentrated. Trituration with ether/hexane gave 2.84 g (56%) of product as a white solid. An analytical sample was recrystallized from ether/hexane, mp 111°–113° C.

¹H NMR (DMSO-d₆) δ1.24 (t, J=6.9 Hz, 3H), 2.15 (s, 3H), 2.24 (s, 3H), 3.84 (q, J=6.9 Hz, 2H), 4.18 (d, J=1.7 Hz, 1H), 4.50 (d, J=6.2 Hz, 2H), 4.53 (d, J=1.7 Hz, 1H), 6.91 (t, J=6.2 Hz, 1H), 7.22 (d, J=8.3 Hz, 2H), 7.46 (d, J=8.3 Hz, 2H).

Anal. calcd for C₁₇H₂₀BrN₃O: C, 56.36; H, 5.56; N, 11.60; Found: C, 56.64; H, 5.64; N, 11.48.

Step 5

Methyl(4-(4-bromobenzylamino)-2,6-dimethylpyrimidin-5-yl)ketone

A solution of 4-(4-bromobenzylamino)-2,6-dimethyl-5-(1-ethoxyvinyl)pyrimidine (2.72 g, 7.51 mmol), 1N HCl (8.3 mL), and acetone (8 mL) was heated under reflux for 2.5 h. The acetone was removed under reduced pressure and the aqueous phase was adjusted to pH 4 with 1N KOH. The resultant white precipitate was collected by filtration to give 2.24 g (89%) of product as a white solid. An analytical sample was recrystallized from hexane, mp 78°–80° C.

¹H NMR (DMSO-d₆) δ2.30 (s, 3H), 2.36 (s, 3H), 2.50 (s, 3H), 4.57 (d, J =5.8 Hz, 2H), 7.25 (d, J=8.3 Hz, 2H), 7.49 (d, J=8.3 Hz, 2H), 8.34 (t, J=5.8 Hz, 1H).

Anal. calcd for C₁₅H₁₆BrN₃O: C, 53.91; H, 4.83; N, 12.57; Found: C, 53.87; H, 4.77; N, 12.55.

Step 6

Methyl[2,6-dimethyl-4-[(2'-(1-tert-butyl- 1H-tetrazol-5-yl)biphenyl- 4-ylmethyl)amino]pyrimidin-5-yl]ketone To a heated solution of methyl(4-(4-bromobenzylamino)-2,6-dimethylpyrimidin-5-yl)ketone (1.67 g, 5.00 mmol) and tetrakis(triphenylphosphine) palladium(0) (0.29 g, 0.25 mmol) in toluene (20 mL) was added a partial solution of 2-[(1-tert-butyl)-1H-tetrazol-5-yl]phenylboronic acid (1.50 g, 6.10 mmol) (prepared according to J. W. Ellingboe, et al. U.S. Pat. No. 5,149,699) and Na₂CO₃ (1.06 g, 10.00 mmol) in water (10 mL) and EtOH (5 mL) in several portions over 1 h. Heating was continued for 2.5 h. The mixture was diluted with EtOAc and the layers were separated. The organic phase was washed with 0.1N NaOH, brine, dried MgSO₄) and concentrated. Purification by flash chromatography (40–50% EtOAc/hexane) and trituration with hexane gave 1.71 g (75% ) of product as a white solid. An analytical sample was recrystallized from ether, mp 131°–132° C.

¹H NMR (CDCl₃) δ1.54 (s, 9H), 2.51 (s, 3H), 2.56 (s, 3H), 2.64 (s, 3H), 4.71 (d, J=5.7 Hz, 2H), 7.12 (d, J=8.3 Hz, 2H), 7.22 (d, J=8.3 Hz, 2H), 7.45 (m, 3H), 7.88 (m, 1H), 9.0 (br s, 1H).

Anal. calcd for C₂₆H₂₉N₇O: C, 68.55; H, 6.42; N, 21.52; Found: C, 68.56; H, 6.40; N, 21.19.

Step 7

2,4-Dimethyl-5-hydroxy-8-[2'-(1-tert-butyl- 1H-tetrazol-5-yl)biphenyl- 4-ylmethyl]-8H-pyrido[2,3-dipyrimidin-7-one To a heated suspension of NaH (60% dispersion in mineral oil; 0.24 g, 5.93 mmol) in diethyl carbonate (1.40 g, 11.85 mmol) and THF (10 mL) was added a solution of methyl[2,6-dimethyl-4-[(2'-(1-tert-butyl- 1H-tetrazol-5-yl)biphenyl- 4-ylmethyl)amino]pyrimidin-5-yl]ketone (1.08 g, 2.37 mmol) in THF (10 mL) over 10 min. Heating was continued for 1.5 h. The mixture was concentrated, taken up in water, and extracted twice with ether (discarded). The aqueous phase was acidified to pH 4 and the precipitate was collected by filtration to give 965 mg (85%) of product. An analytical sample was recrystallized from acetone, mp 235°–237° C.

¹H NMR (CDCl₃) δ1.47 (s, 9H), 2.72 (s, 3H), 2.89 (s, 3H), 5.52 (s, 2H), 6.18 (s, 1H), 7.04 (d, J=8.2 Hz, 2H), 7.31 (d, J=8.2 Hz, 2H), 7.44 (m, 3H), 7.84 (m, 1H).

Anal. calcd for C₂₇H₂₇N₇O₂: C, 67.34; H, 5.65; N, 20.36; Found: C, 66.97; H, 5.58; N, 20.06 .

Step 8

2,4-Dimethyl-5-hydroxy-8-[2'-(1H-tetrazol-5-yl)biphenyl-4-ylmethyl]-8H-pyrido[2,3-d]pyrimidin-7-one Sesquihydrate A mixture of 2,4-dimethyl-5-hydroxy-8-[2'-(1-tert-butyl-1H-tetrazol-5-yl)biphenyl-4-ylmethyl]-8H-pyrido[2,3-d]pyrimidin-7-one (925 mg, 1.92 mmol), methanesulfonic acid (1.84 g, 19.2 mmol), and toluene (10 mL) was heated under reflux for 28 h. 1N KOH (25 mL) was added and the mixture was extracted twice with EtOAC (discarded). The aqueous phase was acidified to pH 4 with 1N HCl and the precipitate (560 mg) was collected by filtration. Recrystallization from EtOH/water gave 424 mg (52%) of product as an off-white solid, mp 278–280 (dec).

$^1$H NMR (DMSO-$d_6$) δ2.55 (s, 3H), 2.80 (s, 3H), 5.43 (s. 2H), 5.86 (s, 1H), 6.99 (d, J=8.1 Hz, 2H), 7.14 (d, J=8.1 Hz, 2H), 7.42 (m, 1H), 7.47 (dd, J=7.7, 1.5 Hz, 1H), 7.54 (m, 1H), 7.58 (dd, J=7.5, 1.5 Hz, 1H).

Anal. calcd for $C_{23}H_{19}N_7O_2 \cdot 1.5H_2O$: C, 61.05; H, 4.90; N, 21.67; Found: C, 60.74; H, 4.94; N, 21.25.

Example 5

2,4-Dimethyl-6-hydroxy-8-[2'-(1H-tetrazol-5-yl) biphenyl-4-ylmethyl]- 5,8-dihydro-6H-pyrido[2,3-d]pyrimidin-7-one Step 1

2,4-Dimethyl-8-[2'-(1-triphenylmethyl-1H-tetrazol-5-yl) biphenyl-4-ylmethyl]- 5,8-dihydro-6H-pyrido[2,3-d]pyrimidin-7-one To a solution of 2,4-dimethyl-8-[2'-(1H-tetrazol-5-yl)biphenyl-4-ylmethyl]-5,8-dihydro-6H-pyrido[2,3-d]pyrimidin-7-one (2.00 g, 4.86 mmol) (prepared according to J. W. Ellingboe, et al. U.S. Pat. No. 5,149,699) in $CHCl_3$ (50 mL) was added triethylamine (0.49 g, 4.86 mmol) and triphenylmethyl chloride (1.36 g, 4.86 mmol). After 2.5 days, the mixture was washed with 0.1N NaOH, brine, dried $MgSO_4$), and concentrated to give a white foam. Trituration with hexane gave 2.64 g (85%) of product as a white solid, mp 160°–161° C.

$^1$H NMR (DMSO-$d_6$) δ2.35 (s, 3H), 2.36 (s, 3H), 2.66 (t, J=7.8 Hz, 2H), 2.82 (t, J=7.8 Hz, 2H), 5.15 (s, 2H), 6.81 (d, J=6.9 Hz, 6H), 6.98 (d, J= 8.1 Hz, 2H), 7.14 (d, J=8.1 Hz, 2H), 7.31 (m, 9H), 7.41 (d, J=7.6 Hz, 1H), 7.55 (m, 2H), 7.77 (d, J=7.2 Hz, 1H).

Anal. calcd for $C_{42}H_{35}N_7O$: C, 77.16; H, 5.40; N, 15.00; Found: C, 77.32; H, 5.34; N, 14.86.

Step 2

2,4-Dimethyl-6-hydroxy-8-[2'-(1H-tetrazol-5-yl)biphenyl-4-ylmethyl]-5,8-dihydro-6H-pyrido[2,3-d]pyrimidin-7-one To a cooled (−78° C.) solution of 2,4-dimethyl-8-[2'-(1-triphenylmethyl-1H-tetrazol-5-yl)biphenyl-4-ylmethyl]-5,8-dihydro-6H-pyrido[2,3-d]pyrimidin-7-one (1.57 g, 2.41 mmol) in THF (5 mL) was added 0.5M potassium hexamethyldisilazide in toluene (5.5 mL, 2.75 mmol). After 45 min, a solution of (+)-camphorsulfonyloxaziridine in THF (5 mL) was added. The mixture was allowed to warm to 5° C. over 5 h. Water (2 mL) and $CF_3CO_2H$ (2 mL) were added and stirring was continued for 1 h. 1N NaOH (30 mL) was added and the mixture was extracted with EtOAc (discarded). The aqueous phase was acidified to pH 4 with 1N HCl and extracted with $CHCl_3$. The extracts were dried $MgSO_4$) and concentrated. Purification by flash chromatography (5–10% MeOH/$CHCl_3$) gave 377 mg of a yellow oil. Crystallization from acetone yielded 234 mg (23%) of product as an off-white solid, mp 154°–156° C.

$^1$H NMR (DMSO-$d_6$) δ2.37 (s, 3H), 2.46 (s, 3H), 2.80 (dd, J=15.8, 10.7 Hz, 1H), 3.11 (dd, J=15.8, 6.2 Hz, 1H), 4.34 (m, 1H), 5.12 (d, J=14.9 Hz, 1H), 5.20 (d, J=14.9 Hz, 1H), 5.92 (d, J=5.2 Hz, 1H), 7.01 (d, J=8.3 Hz, 2H), 7.10 (d, J=8.3 Hz, 2H), 7.28 (dd, J=6.8, 2.1 Hz, 1H), 7.35 (m, 2H), 7.50 (dd, J= 7.3, 1.7 Hz, 1H).

Example 6

5-Hydroxy-2,4-dimethyl-8-[2'-(1H-tetrazol-5-yl)-biphenyl-4-ylmethyl]-6,8-dihydro-5H-pyrido[2,3-d]pyrimidine-7-one Hydrate 0.4 Etherate To a cooled (0° C.), mechanically stirred mixture of 2,4-dimethyl-8-[2'-(1H-tetrazol-5-yl)biphenyl-4-ylmethyl]-5,8-dihydro-6H-pyrido[2,3-d]pyrimidin-7-one (8.2 g, 0.020 mol) (prepared according to J. W. Ellingboe, et al. U.S. Pat. No. 5,149,699), $MgSO_4$ (14.4 g, 0.120 mol) and water (285 mL) was added 2.5N NaOH (8.78 mL). The resultant mixture was adjusted to pH 7.0–7.5 with 2N HCl (0.7 mL). A solution of $KMnO_4$ (6.3 g, 0.040 mol) in water (362 mL) was added dropwise over 2 h 40 min. and the mixture was allowed to warm to room temperature. After 24 h, additional $MgSO_4$ (5.04 g, 0.042 mol) and $KMnO_4$ (2.2 g, 0.014 mol) were added and stirring was continued for 24 h. The reaction mixture was filtered through Solka Floc and the filtrate was concentrated to about 200 mL. The pH was adjusted to about 4 with $KH_2PO_4$ (13.6 g) and the precipitate was collected by filtration. The material was taken up in methanol and filtered to give 1.96 g. The $MnO_2$ recovered by filtration through Solka Floc was stirred in water (400 mL) and filtered. The filtrate was treated with $KH_2PO_4$ to bring the pH to 4 and the precipitate was collected by filtration. The material was taken up in methanol and filtered to give 1.36 g. The combined material was purified by flash chromatography (10–30% MeOH/$CHCl_3$), trituration with EtOAc and MeOH, and trituration with water to give 0.67 g (8%) of product as a white solid, mp 154°–167° C.

Anal. calcd for $C_{23}H_{21}N_7O_2 \cdot H_2O \cdot 0.4\ C_4H_{10}O$: C, 62.18; H, 5.73; N, 20.64; Found: C, 62.24; H, 5.73; N, 20.41.

What is claimed is:

1. A compound of formula I

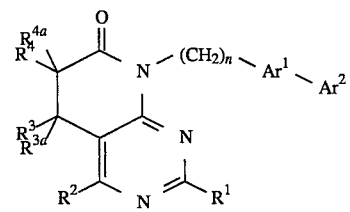

wherein n is 0 to 3;

$R^1$ and $R^2$ are, independently, H, $C_1$–$C_6$alkyl, hydroxy $C_1$–$C_6$alkyl, formyl, $C_1$–$C_6$alkylcarbonyl, carboxy, or carboxy$C_1$–$C_6$alkyl;

$R^3$ and $R^4$ are, independently, H, $C_1$–$C_6$alkyl, or hydroxy;

$R^{3a}$ and $R^{4a}$ are H, or one of —$CR^3R^{3a}$ and —$CR^4R^{4a}$ is a carbonyl group;

with the proviso that at least one of the groups $R^1$ and $R^2$ must be hydroxy$C_1$–$C_6$alkyl, formyl, $C_1$–$C_6$alkylcarbonyl, carboxy, or carboxy$C_1$–$C^6$alkyl; or one of $R_3$ and $R^4$ must be hydroxy; or one of —$CR^3R^{3a}$ and —$CR^4\ R^{4a}$ must be a carbonyl group;

$Ar^1$ is

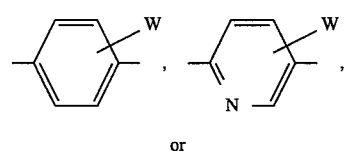

or

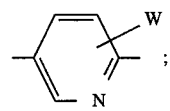

wherein W is H, $C_1$–$C_6$alkyl, halogen, hydroxy, or $C_1$–$C_6$alkoxy;

Ar² is

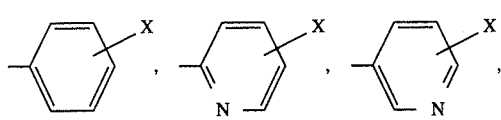

or

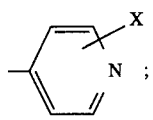

wherein X is

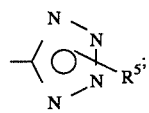

wherein R⁵ is H, CH₃, tert-butyl, tri-n-butylstannyl, or triphenylmethyl; or a tautomer of said compound,
or a pharmaceutically acceptable salt of said compound or tautomer.

2. A compound according to claim 1 which is 2-methyl-7-oxo-8-[2'-(1H-tetrazol-5-yl)biphenyl-4-ylmethyl]-5,6,7,8-tetrahydropyrido[2,3-d]pyrimidine-4-carbaldehyde or a pharmaceutically acceptable salt thereof.

3. A compound according to claim 1 which is 2-hydroxymethyl-4-methyl-8-[2'-(1H-tetrazol-5-yl)biphenyl-4-ylmethyl]-5,8-dihydro-6H-pyrido[2,3-d]pyrimidin-7-one or a pharmaceutically acceptable salt thereof.

4. A compound according to claim 1 which is 4-hydroxymethyl-2-methyl-8-[2'-(1H-tetrazol-5-yl)biphenyl-4-ylmethyl]-5,8-dihydro-6H-pyrido[2,3-d]pyrimidin-7-one or a pharmaceutically acceptable salt thereof.

5. A compound according to claim 1 which is 2,4-dimethyl-5-hydroxy-8-[2'-(1H-tetrazol-5-yl)biphenyl-4-ylmethyl]-8H-pyrido[2,3-d]pyrimidin-7-one or a pharmaceutically acceptable salt thereof.

6. A compound according to claim 1 which is 2,4-dimethyl-5-hydroxy-8-[2'-(1H-tetrazol-5-yl)biphenyl-4-ylmethyl]-6,8-dihydro-5H-pyrido[2,3-d]pyrimidin-7-one or a pharmaceutically acceptable salt thereof.

7. A compound according to claim 1 which is 2,4-dimethyl-6-hydroxy-8-[2'-(1H-tetrazol-5-yl)biphenyl-4-ylmethyl]-5,8-dihydro-6H-pyrido[2,3-d]pyrimidin-7-one or a pharmaceutically acceptable salt thereof.

8. A compound according to claim 1 of formula III

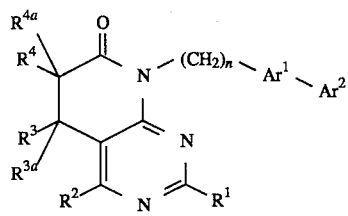

wherein
n is 1;
R¹ and R² are, independently, H, methyl, hydroxymethyl, or formyl;
R³ and R⁴ are, independently, H or hydroxy;

$R^{3a}$ and $R^{4a}$ are H, or one of —CR³R$^{3a}$ and —CR⁴R$^{4a}$ is a carbonyl group;
with the proviso that at least one of the groups R¹ and R² must be hydroxymethyl or formyl; or one of R³ and R⁴ must be hydroxy, or one of—CR³R$^{3a}$ and —CR⁴R$^{4a}$ must be a carbonyl group;
Ar¹ is

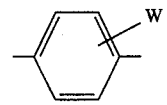

wherein W is H;
Ar² is

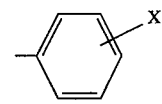

wherein X is

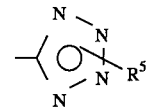

wherein R⁵ is H, CH₃, tert-butyl, or triphenylmethyl; or a tautomer of said compound,
or a pharmaceutically acceptable salt of said compound or tautomer.

9. A compound of formula II

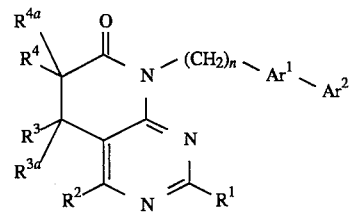

wherein
n is 1;
R¹ and R² are independently H, methyl, ethyl, propyl, isopropyl, hydroxymethyl, 1-hydroxyethyl, 1-hydroxypropyl, 1-hydroxybutyl, 1-hydroxyisobutyl, formyl, methylcarbonyl, ethylcarbonyl, propylcarbonyl, butylcarbonyl, carboxy, carboxymethyl, carboxyethyl, carboxypropyl, or carboxybutyl;
R³ and R⁴ are, independently, H, methyl, ethyl, propyl, or hydroxy;
$R^{3a}$ and $R^{4a}$ are H, or one of —CR³R$^{3a}$ and —CR⁴R$^{4a}$ is a carbonyl group; with the proviso that at least one of the groups R¹ and R² must be hydroxymethyl, 1-hydroxyethyl, 1-hydroxypropyl, 1-hydroxybutyl, 1-hydroxyisobutyl, formyl, methylcarbonyl, ethylcarbonyl, propylcarbonyl, butylcarbonyl, carboxy, carboxymethyl, carboxyethyl, carboxypropyl, or carboxybutyl; or one of R³ and R⁴ must be hydroxy, or one of —CR³R$^{3a}$ and —CR⁴R$^{4a}$ must be a carbonyl group;
Ar¹ is

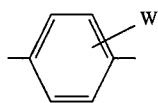

wherein W is H, lower $C_1$–$C_6$ alkyl, halogen, hydroxy, or $C_{1-C6}$ alkoxy;

$Ar^2$ is

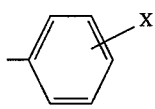

wherein X is $CO_2H$, or

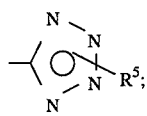

wherein $R^5$ is H, $CH_3$, tert-butyl, tri-n-butylstannyl, or triphenylmethyl; or a tautomer of said compound, or a pharmaceutically acceptable salt of said compound or tautomer.

10. A compound according to claim 9 selected from 2-methyl-7-oxo-8-[2'-(1H-tetrazol-5-yl)biphenyl-4-ylmethyl]- 5,6,7,8-tetrahydropyrido[2,3-d]pyrimidine-4-carbaldehyde;

2-hydroxymethyl-4-methyl-8-[2'-(1H-tetrazol-5-yl)biphenyl-4-ylmethyl]-5,8-dihydro-6H-pyrido[2,3-d]pyrimidin-7-one;

4-hydroxymethyl-2-methyl 8-[2'-(1H-tetrazol-5-yl )biphenyl-4-ylmethyl]- 5,8-dihydro-6H-pyrido[2,3-d]pyrimidin-7-one;

2,4-dimethyl-5-hydroxy-8-[2'-(1H-tetrazol-5-yl)biphenyl-4-ylmethyl]-8H-pyrido[ 2,3-d]pyrimidin-7-one;

2,4-dimethyl-5-hydroxy-8-[2'-(1H-tetrazol-5-yl)biphenyl-4-ylmethyl]-6,8-dihydro-5H-pyrido[2,3-d]pyrimidin-7-one; and 2,4-dimethyl-6-hydroxy-8-[2'-(1H-tetrazol-5-yl)biphenyl-4-ylmethyl]-5,8-dihydro-6H-pyrido[2,3-d]pyrimidin-7-one, or a pharmaceutically acceptable salt or tautomer of such selected compound.

11. A method of treating hypertension in a warm-blooded animal comprising administering to such animal a compound in claim 1 in an amount effective to lower the animal's blood pressure.

12. A method of treating hypertension according to claim 11 wherein the compound is selected from 2,4-dimethyl-5-hydroxy-8-[2'-(1H-tetrazol- 5-yl)biphenyl-4-ylmethyl]-8H-pyrido[2,3-d]pyrimidin-7-one and 2,4-dimethyl-5-hydroxy-8-[2'-(1H-tetrazol- 5-yl)biphenyl-4-ylmethyl]-6,8-dihydro(-5H-pyrido[2,3-d]pyrimidin-7-one, or a pharmaceutically acceptable salt thereof.

13. A method of treating congestive heart failure in a warm-blooded animal comprising administering to such animal a compound in claim 1 in an amount effective to correct the hemodynamic burden on the heart to relieve the congestion.

14. A method of treating congestive heart failure according to claim 13 wherein the compound is selected from 2,4-dimethyl-5-hydroxy-8-[2'-(1H-tetrazol-5-yl)biphenyl-4-ylmethyl]-8H-pyrido[2,3-d]pyrimidin-7-one and 2,4-dimethyl- 5-hydroxy-8-[2'-(1H-tetrazol-5-yl)biphenyl-4-ylmethyl]-6,8-dihydro-5H-pyrido[ 2,3-d]pyrimidin-7-one, or a pharmaceutically acceptable salt thereof.

15. A method of preventing restenosis in a warm-blooded animal in need thereof comprising administering to such animal a compound in claim 1 in an amount effective to prevent restenosis.

* * * * *